United States Patent [19]

Pawelek

US005126125A

[11] Patent Number: 5,126,125

[45] Date of Patent: Jun. 30, 1992

[54] DECREASING THE MELANIN CONTENT IN MAMMALIAN SKIN AND HAIR USING 5,6-DIHYDROXINDOLE DERIVATIVES

[75] Inventor: John M. Pawelek, Hamden, Conn.

[73] Assignee: Yale University, New Haven, Conn.

[21] Appl. No.: 417,987

[22] Filed: Oct. 6, 1989

[51] Int. Cl.$^5$ .................. A61K 7/00; A61K 7/135; A61K 31/405; C07D 209/10

[52] U.S. Cl. ..................... 424/62; 424/D163; 424/401; 514/844; 514/880; 514/415; 548/441

[58] Field of Search ................ 424/62, 59-60

[56] References Cited

U.S. PATENT DOCUMENTS

| 4,595,765 | 6/1986 | Murphy | 548/491 |
| 4,822,375 | 4/1989 | Lang | 548/414 |
| 4,859,668 | 8/1989 | Noga | 514/231.2 |

OTHER PUBLICATIONS

J. M. Pawelek and A. B. Lerner, "5,6-Dihydroxyindole is a Melanin Precursor Showing Potent Cytotoxicity", Nature, 276, 627–628, (1978).

J. M. Pawelek and M. Murray, "Increase in Melanin Formation and Promotion of Cytotoxicity in Cultured Melanoma Cells Caused by Phosphorylated Isomers of L-Dopa", Cancer Research, 46, 493–497, (1986).

A. Korner, and J. Pawelek, "Mammalian Tyrosinase Catalyzes Three Reactions in the Biosynthesis of Melanin", Science, 217, 1163–1165, (1982).

J. Pawelek, A. Korner, A. Bergstrom and J. Bolognia, "New Regulators of Melanin Biosynthesis and the Autodestruction of Melanoma Cells", Nature, 286, 617–619, (1980).

J. M. Pawelek, "Factors Regulating Growth and Pigmentation of Melanoma Cells", J. Invest. Derm., 66, 201–209, (1976).

J. McLane, M. Osber and J. M. Pawelek, "Phosphorylated Isomers of L-Dopa Stimulate MSH Binding Capacity and Responsiveness to MSH in Cultured Melanoma Cells", BBRC, 145, 719–725.

*Primary Examiner*—Thurman K. Page
*Assistant Examiner*—E. J. Webman
*Attorney, Agent, or Firm*—Sprung, Horn Kramer & Woods

[57] ABSTRACT

A method of decreasing the melanin content in mammalian skin and hair by administering to a mammal a composition comprising an effective amount of one or more derivatives of 5,6-dihydroxyindole, the derivatives having one or more substituents which are capable of being removed enzymatically, in admixture with a pharmaceutically acceptable carrier, the amount being 0.5% to 20% wt/wt based on the composition.

12 Claims, No Drawings

DECREASING THE MELANIN CONTENT IN MAMMALIAN SKIN AND HAIR USING 5,6-DIHYDROXINDOLE DERIVATIVES

BACKGROUND OF THE INVENTION

1. Field of the Invention

The present invention concerns decreasing the melanin content in mammalian skin and hair by administering an effective melanin decreasing amount of one or more various derivatives of 5,6-dihydroxyindole (DHI) to a mammal, e.g., a human.

BACKGROUND INFORMATION

J. M. Pawelek and A. B. Lerner, "5,6-Dihydroxyindole Is A Melanin Precursor Showing Potent Cytotoxicity", Nature, 276, 627–628, (1978) shows that at high enough concentrations, the intermediates in melanin biosynthesis are toxic to cells producing pigment. The article also shows that 5,6-dihydroxyindole ("DHI") is far more toxic than L-dopa or tyrosine.

The intermediates in melanin biosynthesis are shown in FIG. 1 of J. M. Pawelek and M. Murray, "Increase in Melanin Formation and Promotion of Cytotoxicity in Cultured Melanoma Cells Caused By Phosphorylated Isomers of L-Dopa", Cancer Research, 46, 493–497, (1986). It is noted that in this FIG. 1 that DHI is synthesized from L-tyrosine or L-dopa in multiple reactions catalyzed by the enzyme tyrosinase. Tyrosinase is a key enzyme in pigment production and when it interacts with its various substrates (including DHI—see A. Korner and J. Pawelek, "Mammalian Tyrosinase Catalyzes Three Reactions in the Biosynthesis of Melanin", Science, 217, 1163–1165, (1982)) free radicals are produced with resultant toxicity to the cells.

Since pigment cells contain tyrosinase and other cells do not, this is likely the reason that the intermediates in melanin biosynthesis are selectively toxic to pigment cells.

The toxicity of melanin intermediates is also discussed in the following articles: J. Pawelek, A. Korner, A. Bergstrom and J. Bolognia, "New Regulators of Melanin Biosynthesis and the Autodestruction of Melanoma Cells", Nature, 286, 617–619, (1980) and J. M. Pawelek, "Factors Regulating Growth and Pigmentation of Melanoma Cells", J. Invest. Derm., 66, 201–209, (1976), J. McLane, M. Osber and J. M. Pawelek, "Phosphorylated Isomers of L-Dopa Stimulate MSH Binding Capacity and Responsiveness to MSH in Cultured Melanoma Cells", BBRC, 145, 719–725, (1987) shows that the effects are a matter of concentration.

DHI is highly unstable in the presence of oxygen and cannot be easily used in a cosmetic cream. It oxidizes into melanin spontaneously within a few minutes when exposed to air. Thus for it to be an effective depigmenting agent it must be derivatized to stabilize it.

European application 239,826 outlines methods for derivatizing DHI into compounds which are stable in air. EP 239,826 describes that derivatized DHI will be an effective pigmenting agent at concentrations from 0.01–15% wt/wt in various delivery compositions (see p. 5, bottom). There is no mention in EP 239,826 concerning depigmentation.

Depigmenting agents now commercially available are hydroquinone, used at 1–2% for OTC sales in products such as "PROCELANA" cream and 4% by prescription. Monobenzylether of hydroquinone is used by prescription in products such as "BENEQUIN" at 20%.

SUMMARY OF THE INVENTION

It is an object of the present invention to provide methods to decrease the melanin content in mammalian skin and hair.

The above object and other objects, aims and advantages are satisfied by the present invention which provides a method of decreasing the melanin content in mammalian skin and hair by administering to a mammal, e.g., a human, a composition comprising an effective melanin decreasing amount of one or more derivatives of 5,6-dihydroxyindole, the derivatives having one or more substituents which are capable of being removed enzymatically, in admixture with a pharmaceutically acceptable carrier, said amount being 0.5% to 20% wt/wt, based on the total composition. The degree of depigmentation will depend on the concentration and frequency of application of the derivative of 5,6-dihydroxyindole. Using a concentration of a derivative of 5,6-dihydroxyindole, e.g., 0.01 to 0.05% wt/wt or perhaps a lower concentration, will result in pigmentation.

DETAILED DESCRIPTION OF THE INVENTION

The 5,6-dihydroxyindole derivative for use in the present invention has one or more substituents which are capable of being removed enzymatically. A non-limiting list of enzymes for removing such substituents include phosphatases, esterases and acetylases.

Preferred 5,6-dihydroxyindole derivatives for use in the present invention are represented by the formula

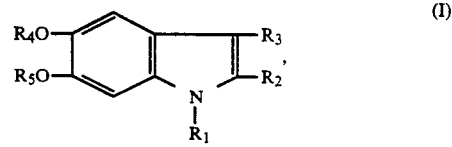

wherein $R_1$ is a hydrogen atom, a lower alkyl group or a $-SiR_9R_{10}R_{11}$ group $R_2$ and $R_3$ are identical or different and are a hydrogen atom, a lower alkyl group, a carboxyl group, a lower alkoxycarbonyl group or a $COOSiR_9R_{10}R_{11}$ group;

$R_4$ and $R_5$ are identical or different and are a hydrogen atom, a linear or branched $C_1$–$C_{20}$ alkyl group, a formyl group, a linear or branched $C_2$–$C_{20}$ acyl group, a linear or branched $C_3$–$C_{20}$ alkenoyl group, a $R_6$—$OSO_2$— group, an $-SiR_9R_{10}R_{11}$ group, a $-P(O)(OR_6)_2$ group, an aralkyl group, or $R_4$ and $R_5$, with the oxygen atoms to which they are bonded, form a ring, optionally containing a carbonyl group when at least one of the groups $R_1$, $R_2$, or $R_3$ is different from hydrogen, or a thiocarbonyl group, a $-P(O)OR_6$ group, a $-CR_7R_8$ group or a methylene group, $R_6$ is a hydrogen atom or a lower alkyl group, $R_7$ is a lower alkoxy group or a mono- or dialkylamino group, and $R_9$, $R_{10}$ or $R_{11}$ are identical or different and are linear or branched lower alkyl groups, at least one of the substituents $R_1$, $R_2$, $R_3$, $R_4$, $R_5$ being different from hydrogen, and pharmaceutically acceptable salts thereof, e.g., salts with alkaline metals, ammonium alkaline earths or amines.

In formula (I) above the lower alkyl or alkoxy group preferably has 1 to 6 carbon atoms.

In formula (I), the alkyl, alkoxy, alkoxycarbonyl, alkenoyl and acyl groups can be substituted, for example, by a halogen (e.g., chlorine, fluorine, bromime or iodine), a nitro group or an amino group.

In formula (I) above, aralkyl is

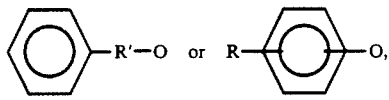

where R' is a $C_1$–$C_{20}$ alkyl and wherein

can be substituted, for example, by a halogen, e.g., chlorine, bromine, fluorine or iodine, a $C_1$–$C_{20}$ alkyl, a nitro group, an amino group or $C_1$–$C_{20}$ alkoxy.

In preferred compounds of formula (I), $R_1$ is hydrogen,
$R_2$ and $R_3$ are identical or different and represent a hydrogen atom or a lower alkyl group,
at least one of the groups $R_4$ or $R_5$ represents a linear or branched $C_1$–$C_{20}$ alkyl group, a linear or branched $C_2$–$C_{20}$ acyl group or a linear or branched $C_2$–$C_{20}$ alkenoyl group, with the other substituent being hydrogen or, also, $R_4$ and $R_5$ simultaneously represent —$SiR_9R_{10}R_{11}$ in which $R_9$, $R_{10}$, $R_{11}$ are as defined above.

Non-limiting examples of compounds encompassed by formula I are as follows: 5,6-dibenzyloxy indole, 5-benzyloxy-6-methoxy indole, 6-benzyloxy-5-methoxy indole, 6-hydroxy-5-methoxy indole, 5-hydroxy-6-methoxy indole, 5,6-diacetoxy indole, 6-acetoxy-5-methoxy indole, (5 or 6)-acetoxy-(6 or 5)-methoxy indole, 5,6-dibenzyloxy-2-carbethoxy indole, 5,6-dibenzyloxy-2-carboxy indole, 5,6-dihydroxy-2-carbethoxy indole, 5,6-dihydroxy-2-carboxy indole, 5,6-dibenzyloxy-2-methyl indole, 5,6-dihydroxy-2-methyl indole, 5,6-dibenzyloxy-3-methyl indole, 5,6-dihydroxy-3-methyl indole, (5 or 6)-formyloxy-(6 or 5)-hydroxy indole, (5 or 6)-acetoxy-(6 or 5)-formyloxy indole, 6-formyloxy-5-methoxy indole, 6-benzyloxy-5-butoxy indole, 5-butoxy-6-hydroxy indole, 5-benzyloxy-6-butoxy indole, 6-butoxy-5-hydroxy indole, (5 or 6)-hydroxy-(6 or 5)-trimethylsilyloxy indole, 5,6-ditrimethylsilyloxy indole, 5,6-[1,1-(1-ethoxy ethyl)dioxy]indole, cyclic 5,6-dihydroxy phosphodiester indole, 5,6-thiocarbonyldioxy indole, 5-methoxy-6-trimethylsilyloxy indole, 5,6-di(trimethylsilyloxy)-2-methyl indole, 5,6-carbonyldioxy-2-methyl indole, (5 or 6)-hydroxy-(6 or 5)-myristoyloxy indole, 5,6-dimyristoyloxy indole, (5 or 6)-hydroxy-(6 or 5)-oleoyloxy indole, 5,6-dioleoyloxy indole, 5,6-di(trimethylsilyloxy)-2-carbethoxy indole, 5,6-di(trimethylsilyloxy)-2-trimethylsilyloxycarbonyl indole, 5,6-di(trimethylsilyloxy)-3-methyl indole, 6-hexadecoxy-5-methoxy indole, 6-hexadecoxy-5-hydroxy indole, 5-hexadecoxy-6-hydroxy indole, 5,6-dipivaloyloxy indole, (5 or 6)-hydroxy-(6 or 5)-pivaloyloxy indole, 5,6-dihexanoyloxy indole, (5 or 6)-hexanoyloxy-(5 or 6)-hydroxy indole, 5,6-dibutanoyloxy indole and (5 or 6)-butanoyloxy-(6 or 5)-hydroxy indole.

Preferrably, in the above formula I, $R_4$ and $R_5$, independently of each other are H,

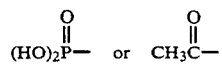

and $R_1$, $R_2$ and $R_3$ are all H.

Pharmaceutically acceptable carriers useful in the practice of the invention are known in the art and include, for injection—distilled water; for controlled release—microcapsules comprising carboxymethylene copolymers; for transdermal release—acrylamides and for topical application—cosmetic bases.

In addition, if desired, the composition according to this embodiment comprises at least one additive selected from the group consisting of solvents, fragrances, perfumes, thickeners, softeners, moisturizers, oils, fats, sealers, emollients, wetting agents, sunscreening protective agents, preservatives, chelating agents, surfactants, polymers, anti-foaming agents, emulsifiers and bactericides.

Cosmetic bases useful in the practice of the invention are all well known and include lotions, creams, gels, emulsions, balms, sticks, oils, milks, ointments and dusting powders. Examples thereof may be found in, e.g., U.S. Pat. Nos. 4,228,151; 4,282,206 and 2,949,403.

Solvents for use in accordance with the invention include, for example, alcohols, e.g., ethanol, isopropyl alcohol and benzyl alcohol, glycols, e.g., ethylene glycol, propylene glycol, dipropylene glycol, terpropylene glycol and monomethyl, monoethyl and monobutyl ethers of ethylene glycol, monoethyl ether acetate of ethylene glycol, distilled and/or deionized water, physiological saline solutions and the like. The specific solvent chosen will depend on the method of application.

The lotions according to the invention may be hydroalcoholic or oleoalcoholic, based on lower alcohols such as ethanol or a glycol, such as propylene-glycol, and esters of fatty acids such as isopropyl myristate.

A proper cosmetic medium is preferably anhydrous. In this invention, a medium is called anhydrous when containing less that 1% water.

The cosmetic medium according to this invention may also contain or be constituted exclusively by fats, that may be chosen among mineral oils such as vaseline oil; animal oils such as whale oil, seal oil, menhaden oil, halibut oil, cod oil, tunafish oil, turtle oil, tallow oil, oil from beef feet, horse feet, sheep feet, mink, otter, marmot, etc.; vegetable oils such as from almond, peanut, colza, wheat germ, olive, corn, jojoba, sesame, sunflower, palm or similar oils.

Non-limiting examples of fats which can be utilized in formulations according to the invention include vaseline, paraffin, hydrogenized lanolin, acetylated lanolin, silicon oils. Waxes that may be used are, among others, sipol wax, lanolin wax, beeswax, candelilla wax, microcrystalline wax, Carnauba wax, sperm oil, cocoa butter, karite butter, silicon wax, oils hydrogenated at 25° C., sucroglycerides, oleates, myristates, linoleates, stearates of calcium, magnesium, zirconium or aluminum. Fatty alcohols that can be used in such formulation are, among others, lauric alcohol, cetylic, myristic, stearic, palmitic and oleic alcohols, eventually polyoxyethylated or polyglycerolated. Examples of fatty polyoxyethylated alcohols include lauric, cetylic, stearylic and oleic alcohols containing from 2 to 20 moles ethylenic oxide.

Particularly preferred as preparations are anhydrous oils and sticks.

Fragrances useful in the preparation of compositions for tanning or sun-tanning or for preventing sun-tanning are known, per se, and need not be discussed further. Such fragrances can be utilized in the compositions for use in the present invention.

It may also be desirable to add a preservative to the compositions utilized in the present invention if they are to be used for topical applications. Preservatives are well known and may be exemplified by methylparaben, "DOWACIL 2000" and propylparaben.

If desired, in order to reduce the acidity or basicity of the compositions, bases, acids or buffers may be added thereto in accordance with the knowledge of the art.

Non-limiting uses for depigmenting agents according to the invention are as follows:

(1) as agents for achieving a more even skin tone in dark-skinned individuals with uneven skin color (as skin "lighteners" in general);
(2) as agents for relieving the symptoms of melasma, a disorder involving hyperpigmentation (melasma is seen in 50–75% of all pregnant women and in up to one-third of women taking birth control pills);
(3) as agents for lightening solar lentigos ("old-age" or "liver spots") which are areas of sun-induced hyperpigmentation associated with the aging process;
(4) as agents for reducing post-imflammatory hyperpigmentation (areas of excess pigmentation that occur after inflammations caused by disorders such as acne) and
(5) as agents for depigmenting patients with severe vitiligo.

The compounds for use in the invention may be prepared following known procedures. The derivatives of 5,6-dihydroxy indole substituted or not in positions 2 and/or 3 may be synthesized starting from substituted compounds in positions 5 and in 6, the last stage of formation being a reducing cyclization of a beta-2-dinitrostyrene derivative or derivatives from 5,6-dihydroxy indole substituted in positions 1, 2 and/or 3 may be synthesized starting from 5,6-dihydroxy indole substituted in position 1, 2 and/or 3 by methods in which the presence of free bases is avoided in the reacting mixture due to the instability in a basic medium of the 5,6-dihydroxy indole substituted in positions 1, 2 and/or 3.

Therefore, one can proceed either by phase transfer in the case of etherification, or by the methods of transesterification in the case of esters of 5,6-dihydroxy indole substituted in positions 1, 2 and/or 3. In latter cases, the monoacylated and diacylated derivatives are separated by a chromatographic column.

The following non-limiting examples concern compounds and formulations according to the invention.

PREPARATION EXAMPLES

EXAMPLE 1

Preparation of 5-Formyloxy 6-hydroxy indole and 6-formyloxy 5-hydroxy indole

To 1.8 g (0.0122 mole) 5,6-dihydroxy indole in solution in 20 ml dry ether is added 2.39 g (0.0257 mole) formyl acetic anhydride, drop by drop, at $-5°$ C. During 6 hours, the temperature is raised gradually to 20° C. It is left stirring overnight. A white precipitate is collected, which is filtered and recrystallized in a toluene-acetone mixture (3/2). The compound is obtained as a white powder: 218 mg (yield: 10%). 5-Formyloxy 6-hydroxy indole and 6-formyloxy 5-hydroxy indole are in a mixture 60/40 of the two formylates as indicated by proton NMR spectrum. MS (70 eV) for $C_9H_7NO_2$: 177 (M+,68%) 149 (100), 120 (17), 103 (45) and 65 (21).

EXAMPLE 2

Preparation of 6-Acetoxy 5-formyloxy indole and 5-acetoxy 6-formyloxy indole

The compound produced by Example 1 (150 mg, $8.5 \times 10^{-4}$ mole) is stirred for 4 hours with 2.25 ml acetic anhydride and 0.12 ml pyridine. After evaporation of the solvents, the procedure is repeated in dichloromethane and successive washings with aqueous solutions of HCl O, IN, 2% NaHCO, and water; drying 6-Acetoxy 5-formloxy indole and 5-acetoxy 6-formyloxy indole are obtained: 150 mg (yield: 80%) which, according to the NMR spectrum, is a mixture 60/40 of the two isomers.

EXAMPLE 3

Preparation of 6-Formyloxy 5-methoxy indole

A solution of 12 g (0.0735 mole) of 6-hydroxy 5-methoxy indole and 12.95 g (0.147 mole) of formyl acetic anhydride in 100 ml toluene is refluxed for 16 hours under nitrogen atmosphere. After cooling, 30 g of silica 60 is added to the reacting medium, and it is filtered and concentrated to half its volume. The white precipitate that is obtained is filtered and then recrystallized in 30 ml toluene. After vacuum-drying, 4.2 g of 6-formyloxy 5-methoxy indole is obtained (white powder, yield 30%).

Analysis: $C_{10}H_9NO_3$:
Calculated: C 62.82; H 4.74; N 8.33.
Found: C 62.84; H 4.75; N 7.29.

EXAMPLE 4

Preparation of 5,6[di(trimethylsilyloxy]indole

To 0.81 g (0.004 mole) of N,O-bis(trimethylsilyl) acetamide is added, stirring at room temperature, 0.3 g (0.002 mole) of 5,6-dihydroxy indole. When dissolution is completed, 2 ml dichloromethane are added and the solution is passed through a column of silica 60, eluating with dichloromethane. The first fraction obtained is concentrated in a rotavapor, then vacuum-dried. Thus are obtained 0.42 g (yield: 71%) of white crytal of 5,6[di(trimethylsilyloxy]indole.

Analysis: $C_{14}H_{23}NO_2Si_2$:
Calculated: C 57.29; H 7.90; N 4.77.
Found: C 57.39; H 7.98; N 4.72.

EXAMPLE 5

Preparation of 5,6[dioxy-1,1(1-ethoxy ethyl)]indole

In a round bottom flask with a distillation equipment one heats 14.6 ml (0.08 mole) of triethylorthoacetate and 3 g (0.02 mole) of 5,6-dihydroxy indole, in an oil bath at 120° C., so as to maintain continuous distillation of the obtained ethanol (reaction time: 4 hours). The excess triethylorthoacetate is distilled and one isolates the fraction with a boiling point 160° C. at $1.06 \times 10^2$Pa. The colorless oil obtained crystallizes into 5,6[dioxy-1,1(1-ethoxy ethyl)]indole. (2.71 g, yield: 62%).

Analysis: $C_{12}H_{13}NO_3$:

Calculated: C 65.74; H 5.98; N 6.39.
Found: C 65.34; H 6.01; N 6.29.

EXAMPLE 6

Preparation of 5-Hydroxy-6-(trimethylsiloxy indole and 6-hydroxy 5-(trimethylsiloxy) indole One stirs for 2¼ hours a solution of 200 ml of dry tetrahydrofurane (THF) containing 3 g (0.02 mole) of 5,6-dihydroxy indole and 8.2 g (0.04 mole) of bis(trimethylsilyl)urea. After addition of 100 ml of toluene, the organic phase is washed with water and after drying on sodium sulfate, it is concentrated in vacuum. The 5 g of residue is passed rapidly through a column of silica (eluent: $CH_2Cl_2$). One recuperates together with di(-trimethylsilyloxy)-5,6 indole, 0.5 g of the 5-hydroxy-6-(trimethylsiloxy) indole and 6-hydroxy 5-(trimethylsiloxy) indole (yield: 11%), a mixture 30/70 of the two monosilylates as indicated by proton NMR spectrum.

Analysis: $C_{11}H_{15}NO_3Si$:
Calculated: C 59.69; H 6.83; N 6.33.
Found: C 59.27; H 6.86; N 6.33.

EXAMPLE 7

Preparation of Cyclic Phosphodiester of 5,6-dihydroxy indole

To a solution of 4.14 g (0.006) of 1,2,3-trizole and 1.84 ml (0.02 mole) of phosphane oxychloride in 150 ml of dry dioxane, one adds, at room temperature, under a nitrogen atmosphere and in the absence of humidity, 8.06 g (0.06 mole) of triethylamine in 15 minutes. One lets it stir for 40 minutes at 20° C. The triethylamine chlorhydrate obtained is filtered, avoiding contact of the filtrate with air. The phosphoryl tris(1,2,3-triazole) solution obtained is added in 2 hours at 20° C. under a nitrogen atmosphere to a solution of 2.68 g (0.018 mole) of 5,6-didhydroxy indole. One then stirs during 3¼ hours, and lets it stand overnight, and the obtained precipitate is filtered (2.9 g dry). This precipitate is stirred for 1 hour at room temperature in 100 ml of water, again filtered and dried. One recuperates the cyclic phosphodiester of 5,6-dihydroxy indole (1 g, yield: 26%).

The NMR spectrum agrees with the expected structure.

EXAMPLE 8

Preparation of 5,6-Thiocarbonyldioxy indole

To a solution of 1.49 g (0.01 mole) of 5,6-dihydroxy indole in 100 ml of isopropylic ether and 50 ml of toluene, one adds, drop by drop at 60° C. and under nitrogen atmosphere, a solution of 2.82 g (0.0158 mole) of thiocarbonyldiimidazole in 400 ml of toluene. It is stirred for 2 hours at 60° C. The reacting mixture is concentrated under vacuum. To the obtained residue, one adds 200 ml of water. The light precipitate is filtered and washed in plenty of water. One dissolves it again in 50 ml of acetone and precipitates it again with 300 ml of water. After vacuum-drying at 13.3 Pa, one obtains 1,2 g (yield: 63%) of 5,6 thiocarbonyldioxy indole (slightly yellow powder).

Analysis $C_4H_5NO_2S$:
Calculated: C 56.56; H 2.64; N 7.33; S 16.77.
Found: C 58.57; H 2.58; N 7.19; S 16.64.

EXAMPLE 9

Preparation of 6-Benzyloxy 5-butoxy indole

One heats for 2 hours under reflux and stirring a mixture of 5-butoxy 4-hydroxy 2-nitro benzaldehyde (31 g, 0.13 mole) of benzyl chloride (20.2 g, 0.18 mole) and of potassium carbonate (22.11 g, 0.16 mole), in 80 ml of dimethylformamide. One pours the reacting mixture in 200 ml ice cold water and filters the precipitate. One obtains after recrystallization in a mixture of hexane-toluene the 4-benzyloxy 5-butoxy 2-nitro benzaldehyde (30.2 g, yield 71%, yellow powder) fusion=94° C.

To a mixture of the previous derivative (26.3 g, 0.08 mole) in 90 ml of glacial acetic acid and dry ammonium acetate (8.85 g, 0.115 mole), one adds nitromethane (10.1 ml, 0.185 mole). After 5 hours of refluxing, one pours the reaction mixture in 200 ml ice cold water. The brown precipitate is filtered and recrystallized in ethanol. One obtains 4-benzyloxy 5-butoxy-2-dinitro, beta-styrene (18.4 g, yield 62%, yellow powder); fusion=152° C.

A solution of 180 ml of absolute ethanol and 80 ml acetic acid is brought to 60° C. To this solution, activated iron is added (48 g); one brings the mixture to 80° to 85° C., stirring well and adds the previously obtained derivative (8.0 g, 0.024 mole) in 15 minutes. After 30 minutes of stirring at 85° C., one filters the ferric muds, rinses them with 300 ml acetic acid, then 300 ml ethanol. The filtrate is diluted with ice. The obtained precipitate is filtered, washed with water and dried. After passing it through a silica 60 column (eluent: $C_2Cl_2$, one recuperates 6-benzyloxy 5-butoxy indole (5 g, yield 70%).

Analysis: $C_{19}H_{21}NO_2$:
Calculated: C 77.26; H 7.16; N 4.74.
Found: C 77.36; H 7.17; N 4.72.

EXAMPLE 10

Preparation of 5-Butoxy 6-hydroxy indole

6-Benzyloxy 5-butoxy indole (4 g, 0.0135 mole) is hydrogenated under 50 atmospheres of hydrogen in a reactor with 40 ml of ethanol and 0.6 g 10% palladium on carbon for 3 hours. After filtration and evaporation of the solvent, the residue is recrystallized in a mixture of benzene-hexane to produce 5-butoxy 6-hydroxy indole (2.5 g, yield 90%).

Analysis $C_{12}H_{19}NO_2$:
Calculated: C 70.22; H 7.37; N 6.82.
Found: C 70.31; H 7.28; N 6.77.

EXAMPLE 11

Preparation of 5-Benzyloxy 6-butoxy indole

To a solution of 28 ml of absolute ethanol and 14 ml of acetic acid, one adds at 60° C. 8.6 g of activated iron. One keeps it 15 minutes at 80° C. and adds the 5-benzyloxy 4-butoxy 2-dinitro, beta-styrene (1.6 g, 0.0043 mole). It is left at 80° C. for one hour, the ferric muds are filtered and then rinsed with 40 ml of ethanol and 40 ml of acetic acid. The filtrate is diluted with 100 ml of ice cold water. After extracting the solution with methylene chloride, and drying it on sodium sulfate from the organic phase, the solution is concentrated and passed through a chromatographic silica 60 column (eluent toluene/$CH_2Cl_2$ 50:50). One obtains 0.5 g (yield 40%) of 5-benzyloxy 6-butoxy indole.

Analysis: $C_{19}H_{21}NO_2$:
Calculated: C 77.26; H 7.16; N 4.74.

Found: C 77.06; H 7.14; N 4.82.

EXAMPLE 12

Preparation of 6-Butoxy 5-hydroxy indole

5-Benzyloxy 6-butoxy indole (0.5 g, 0.0017 mole) is hydrogenated under 50 atmospheres of hydrogen in a reactor with 5 ml of absolute ethanol and 70 mg of 10% palladium on carbon for 2 hours. After filtration and evaporation of the solvent, the residue is purified by chromatography on silica 60 (eluent: $CH_2Cl_2$, to obtain 6-butoxy 5-hydroxy indole (0.19 g, beige powder, yield 55%).

Analysis: $C_{12}H_{19}NO_1$:
Calculated: C 70.22; H 7.37; N 6.82.
Found: C 70.11; H 7.37; N 6.75.

EXAMPLE 13

Preparation of 5-Methoxy 6-trimethyl-silyloxy indole

One mixes at room temperature hydroxy-6-methoxy-5 indole (2.04 g, 0.0125 mole) and $N_3O$-bis(trimethylsilyl)acetamide (5.08 g, 0.025 mole) till completely solubilized. After chromatography on silica 60 (eluent: $CH_2Cl_2$), one obtains 5-methoxy-6-trimethylsiloxy indole (2.54 g, yield 86%).

Analysis: $C_{12}H_{17}NO_2Si$:
Calculated: C 61.24; H 7.28; N 5.95.
Found: C 61.30; H 7.32; N 6.01.

EXAMPLE 14

Preparation of 5,6-Di(trimethylsilyloxy) 2-methyl indole

Dihydroxy-5,6 methyl 2 indole (90 mg, $5.5 \times 10^{-4}$ mole) and N,O-bis(trimethylsilyl)acetamide (220 mg, $1.1 \times 10^{-3}$ mole) are stirred at room temperature till completely solubilized. The obtained product is purified on silica 60 column (eluent: toluene $CH_2Cl_2$ 50:50. One obtained 5,6-di(trimethylsilyloxy) 2-methyl indole.

Analysis: $C_{16}H_{26}NO_2Si_2$:
Calculated: C 58.58; H 8.19; N 4.55.
Found: C 58.54; H 8.18; N 4.6.

EXAMPLE 15

Preparation of 5,6-Carbonyldioxy 2-methyl indole

To dihydroxy-5,6-methyl-2-indole (0.51 g, 0.0031 mole), dissolved in 50 ml isopropyl ether, one adds, refluxing, carbonyldiimidazole (1.67 g, 0.0103 mole) in solution in 300 ml toluene. After 2 hours of refluxing, one adds 200 ml of water and separates the toluenic phase, which is then dried on sodium sulfate. 5,6-Carbonyldioxy 2-methyl indole is obtained (0.45 g, yield 76%).

Analysis: $C_{10}H_7NO_3$:
Calculated: C 63.49; H 3.73; N 7.40.
Found: C 63.44; H 3.75; N 7.06.

EXAMPLES 16 AND 17

Preparation of (5 or 6)-hydroxy (6 or 5)-myristoyloxy indole and 5,6-dimyristoyloxy indole One refluxes for 4 hours a solution of 5,6-dihydroxy indole (2.98 g, 0.02 mole) in 300 ml of THF and in N-myristoylimidazole (5.57 g, 0.02 mole). After concentration in vacuum, the residue is passed through a silica 60 chromatographic column (eluent: $CH_2Cl_2$), resulting in dimyristoyloxy-5,6 indole (2.6 g, yield 23%).

Analysis: $C_{34}H_{49}NO_4$:
Calculated: C 75.88; H 10.44; N 2.46.

Found: C 75.60; H 10.40; N 2.71.

EXAMPLES 18 AND 19

Preparation of (5 or 6)-Hydroxy (6 or 5)-oleoyloxy indole and 5,6-dioleoyloxy indole In a solution of 5,6-dihydroxy indole (2.98 g, 0.02 mole), in 50 ml of tetrahydrofurane, one adds drop by drop, at 20° C. and under a nitrogen atmosphere, N-oleylimidazole in solution in 100 ml of tetrahydrofurane. One refluxes it for 4 hours. The solvent is eliminated under vacuum and the residue is passed through a silica 60 chromatographic column (eluent: toluene/$CH_2Cl_2$ 50:50), resulting in dioleoyloxy-5,6 indole (1.9 g, yield 14).

Analysis: $C_{44}H_{71}N_4$:
Calculated: C 77.94; H 10.55; N 2.08.
Found: C 77.84; H 10.34; N 2.11.
and hydroxy-(5 or 6) oleoxyloxy (6 or 5) indole (eluent: $CH_2Cl_2$) (5 g, yield: 60%), which is a mixture 70/30 of the two monoesters as indicated by proton NMR spectrum.

Analysis: $C_{24}H_{39}NO_3$:
Calculated: C 75.50; H 9.50; N 3.39.
Found: C 75.82; H 9.54; N 3.41.

EXAMPLE 20

Preparation of 5,6-(trimethylsilyloxy-2-carbethoxy indole

Dihydroxy-5,6 methyl-2 indole (442 mg, 0.0002 mole) and N,O-bis(trimethylsilyl)acetamide (814 mg, 0.004 mole) are stirred for 30 minutes. The obtained solution is passed through a silica 60 chromatographic column (eluent: toluene/$CH_2Cl_2$ 50:50). After concentration under vaccum, one obtains 5,6-di(trimethylsilyloxy)-2-carbethoxy indole (0.59 g, yield 73%).

Analysis: $C_{17}H_{27}NO_4Si_2$:
Calculated: C 55.90; H 7.44; N 3.83.
Found: C 55.90; H 7.55; N 3.77.

EXAMPLE 21

Preparation of 5,6-Di(trimethylsilyloxy)-2-trimethylsilyloxy)-2-trimethylsilyloxycarbonyl indole Dihydroxy-5,6 carboxy-2 indole (0.2 g, 0.00103 mole) and N,O-bis(trimethylsilyl) acetamide (2.5 g, 0.0124 mole) are brought to 60° C. for one hour while stirred. The solution is poured in 50 g of ice and the precipitate is filtere and washed in water. It is taken again in the dichloromethane and dried on sodium sulfate. After evaporation under vacuum, one obtains 5,6-di(trimethylsilyloxy)-2-trimethylsilyloxycarbonyl indole (0.35 g, yield 83%).

MS (70 eV) for $C_{18}H_{31}NO_4Si_2$: 409 (M+,(12,5)337(41),319(14),232(30),75(75) and 73(100).

EXAMPLE 22

Preparation of 5,6-Di(trimethylsilyloxy) 3-methyl indole

Acetoxy-(5 or 6)formyloxy-(6 or 5) indole (0.3 g, 0.0018 mole) and N,O-bis(trimethylsilyl) acetamide (0.61 g, 0.0036 mole) are stirred during 30 minutes at room temperature. The obtained solution is passed through a silica 60 chromatographic column (eluent: $CH_2Cl_2$), resulting in 5,6-di(trimethylsilyloxy) 3-methyl indole (0.43 g, yield 78%).

Analysis: $C_{15}H_{25}NO_2Si_2$:

Calculated: C 58.27; H 8.19; N 4.55.
Found: C 58.55; H 8.18; N 4.53.

EXAMPLE 23

Preparation of 6-Hexadecoxy 5-methoxy indole

One introduces, drop by drop, in 20 minutes, hydroxy-6-methoxy-5-indole (2 g, 0.0123 mole) dissolved in 10 ml of dimethylformamide in a mixture of bromo-1 hexadecane (4.5 g, 0.0145 mole) and of potassium carbonate (1.87 g, 0.0135 mole) in 45 ml of DMF at 70° C. and under a nitrogen atmosphere. The reacting mixture is stirred under nitrogen atmosphere at 80° C. for 3½ hours. The blackish mixture is poured, stirring, into ice cold water and the obtained brownish solid is immediately filtered and washed in water. It is taken into dichloromethane and dried on sodium sulfate. After chromatography on silica 60 (eluent toluene/$CH_2Cl_2$ 50:60) and recrystallization in hexane, one obtains 6-hexadecoxy 5-methoxy indole (1.66 g, yield 35%).

Analysis: $C_{25} H_{41} NO_2$:
Calculated: C 77.57; H 10.66; N 3.61.
Found: C 77.35; H 10.62; N 3.71.

EXAMPLES 24 AND 25

Preparation of 6-Hexadecoxy 5-hydroxy indole
5-hexadecoxy 6-hydroxy indole

In 30 ml of dry DMF one introduces successively at 50° C., under a nitrogen atmosphere and stirring, potassium carbonate (2.76 g, 0.02 mole), 5,6-dihydroxy indole (3 g, 0.02 mole) and 1-bromo hexadecane (6.14 g, 0.02 mole). One heats at 60° to 70° C. for 2½ hours. The blackish mixture is poured in ice cold water under strong stirring and the dark brown precipitate is immediately filtered, washed in water, taken up in dichloromethane and dried 5 minutes on sodium sulfate. The solution is concentrated and chromatographed on silica 60 (eluent: toluene/$CH_2Cl_2$ 50:50) to result in hexadecoxy-6-hydroxy-5 indole (1.8 g, yield 24%).

Analysis: $C_{24} H_{39} NO_2$:
Calculated: C 77.16; H 10.52; N 3.75.
Found: C 77.44; H 10.54; N 3.85.
and in hexadecoxy-5-hydroxy-6 indole (0.8 g, yield 11%)

Analysis: $C_{24} H_{39} NO_2$:
Calculated C 77.16; H 10.52; N 3.75.
Found: C 77.07; H 10.59; N 3.91.

EXAMPLES 26 AND 27

Preparation of 5,6-Dipivaloyloxy indole and (5 or 6)-hydroxy (6 or 5)-pivaloyloxy indole)

To a solution of pivalic acid (1.122 g, 0.011 mole) in 25 ml methylene chloride, one adds N,N-carbonyl diimidazole (1.78 g, 0.011 mole). It is stirred at room temperature until the gaseous emanations of $CO_2$ stop (1 hour). Under a nitrogen atmosphere and at room temperature, one adds the 5,6-dihydroxy indole (1.64 g, 0.011 mole), and one stirs it for 4 hours. The organic phase is washed in water and dried on sodium sulfate. After separation on a chromatographic column of silica 60, one obtains dipivaloyloxy-5,6 indole (eluent: toluene/$CH_2Cl_2$ 50:50) (0.50 g, yield 17%).

Analysis: $C_{18} H_{23} NO_4$:
Calculated: C 68.12; H 7.30; N 4.41.
Found: C 68.02; H 7.27; N 4.49.
and hydroxy-(5 or 6) pivaloyloxy-(6 or 5) indole (eluent $CH_2Cl_2$) (1.74 g, yield 68%)

Analysis $C_{13} H_{15} NO_3$:
Calculated: C 68.84; H 6.48; N 6.00;.
Found: C 66.77; H 6.49; N 5.90.

EXAMPLES 28 AND 29

Preparation of 5,6-dihexanoyloxy indole and (5 or 6)-hexanoyloxy (6 or 5)-hydroxy indole Identically as in the previous examples, hexanoic acid (2.65 g, 0.022 mole) is treated in methylene chloride (50 ml) with N,N-carbonyl diimidazole (3.75 g, 0.022 mole) and 5,6-dihydroxy indole (3.28 g, 0.022 mole). One obtains dihexanoyloxy-5,6-indole (1.90 g, yield 25%).

Analysis: $C_{20} H_{27} NO_4$:
Calculated: C 69.54; H 7.89; N 4.05.
Found: C 69.26; H 7.93; N 3.98.
and hexanoyloxy-(5 or 6) hydroxy-(6 or 5) indole (3.21 g, yield 59%).

Analysis $C_{14} H_{17} NO_3$:
Calculated: C 68.00; H 6.93; N 5.66.
Found: C 67.65; H 6.98; N 5.64.

EXAMPLES 30 AND 31

Preparation of 5,6-Dibutanoyloxy indole and (5 or 6)-butanoyloxy (6 or 5) hydroxy indole Identically as in the previous examples, butanoic acid (2.9 g, 0.033 mole) is treated in methylene chloride (75 ml) with N,N-carbonyl diimidazole (5.35 g, 0.033 mole) and 5,6-dihydroxy indole (4.92 g, 0.033 mole). One obtains dibutanoyloxy-5,6 indole (2.77 g, yield 29%).

Analysis: $C_{16} H_{19} NO_4$:
Calculated: C 68.42; H 6.62; N 4.84.
Found: C 66.85; H 6.64; N 4.76.
and butanoyloxy-(5 or 6) hydroxy-(6 or 5) indole (2.64 g, yield 36.5%).

Analysis: $C_{12} H_{13} NO_3$:
Calculated: C 68.73; H 5.98; N 6.38.
Found: C 85.46; H 5.94; N 6.14.

EXAMPLE 32

Milk Formulation

One prepares the following formulation:
0.75 g of hydroxy-6- methoxy-5 indole
oleocetylic alcohol at 30 moles ethylene oxide 7.0 g
stearylic alcohol 4.0 g
isopropyl myristate 4.0 g
vaseline oil 11.0 g
silicon oil 1.0 g
propyleneglycol 5.0 g
sorbitol in aqueous solution at 70% 10.0 g
preservative, fragrances
demineralized water 100 g.

EXAMPLE 33

Cream Formulation

One prepares the following formulation:
0.9 g of hydroxy-6 methoxy-5 indole
sorbitol in aqueous solution at 70% 5.0 g
mixture of mono and distearate of glycerol, sold under the tradename "GELEOL" by Gattefosse 2.0 g
myristic alcohol 6.0 g
oleic alcohol at 20 moles of ethylene oxide 10.0 g
isopropyl myristate 4.0 g
silicon oil 1.0 g
sunflower oil 12.0 g
preservative, fragrances
demineralized water 100 g.

EXAMPLE 34

Gel Formulation

One prepares the following formulation:
0.1 g of diacetoxy-5,6 indole
propyleneglycol 5.0 g
ethyl
hydroethylcellulose, sold under the tradename "CEL-
LOSIZE" PCG10 by Union Carbide 1.5 g
demineralized water 100 g.

It will be appreciated that the instant specification and claims set forth by way of illustration and not limitation, and that various modifications and changes may be made without departing from the spirit and scope of the present invention.

What is claimed is:

1. A method of decreasing the melanin content of human skin or hair which comprises applying thereto an amount effective therefor of a composition containing 0.5 to 20% by wight or at least one derivative of 5,6-dihydroxyindole in admixture with a pharmaceutically acceptable carrier, the 5,6-dihydroxyindole derivative having the formula

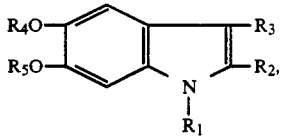

wherein $R_1$ is a hydrogen atom, a lower alkyl group or a $-SiR_9R_{10}R_{11}$ group, $R_2$ and $R_3$ are identical or different and are a hydrogen atom, a lower alkyl group, a carboxyl group, a lower alkoxycarbonyl group or a $COOSiR_9R_{10}R_{11}$ group, $R_4$ and $R_5$, are identical or different and are a hydrogen atom, a linear or branched $C_1-C_{20}$ alkyl group, a formyl group, a linear or branched $C_2-C_{20}$ acyl group, a linear or branched $C_3-C_{20}$ alkenoyl group, a $R_6OSO_2$ group, an $-SiR_9R_{10}R_{11}$ group, a $-P(O)(OR_6)_2$ group, an aralkyl group, or $R_4$ and $R_5$, with the oxygen atoms to which they are bonded, form a ring, optionally containing a carbonyl group when at least one of the groups $R_1$, $R_2$, or $R_3$ is different from hydrogen, or a thiocarbonyl group, a $-P-(O)OR_6$ group, a $-CR_7R_8$ group or a methylene group, $R_6$ is a hydrogen atom or a lower alkyl group, $R_7$ is a lower alkoxy group or a mono- or dialkyl-amino group, and $R_9$, $R_{10}$ or $R_{11}$ are identical or different and are linear or branched lower alkyl groups, at least one of the substituents $R_1$, $R_2$, $R_3$, $R_4$ and $R_5$ being different from hydrogen, and pharmaceutically acceptable salts thereof.

2. A method according to claim 1, wherein the salt is an alkaline metal salt, an ammonium alkaline earth salt or an amine salt.

3. A method according to claim 1, wherein the lower alkyl group has 1 to 6 carbon atoms and the alkoxy group has 1 to 6 carbon atoms.

4. A method according to claim 1, wherein $R_1$ is hydrogen,
$R_2$ and $R_3$ are identical or different and are hydrogen or a lower alkyl group,
at least one of the groups $R_4$ or $R_5$ represents a linear or branched $C_1-C_{20}$ alkyl group, a $C_2-C_{20}$ linear or branched acyl group, a linear or branched $C_2-C_{20}$ alkenoyl group, the other of $R_4$ or $R_5$ being hydrogen or, $R_4$ and $R_5$ simultaneously are $-SiR_9R_{10}R_{11}$ in which $R_9$, $R_{10}$, $R_{11}$ have the meanings indicated in claim 4.

5. A method according to claim 1, wherein the 5,6-dihydroxy indole derivation is 5,6-dibenzyloxy indole, 5-benzyloxy-6-methoxy indole, 6-benzyloxy-5-methoxy indole, 6-hydroxy-5-methoxy indole, 5-hydroxy-6-methoxy indole, 5,6-diacetoxy indole, 6-acetoxy-5-methoxy indole, (5 or 6)-acetoxy-(6 or 5)-methoxy indole, 5,6-dibenzyloxy-2-carbethoxy indole, 5,6-dibenzyloxy-2-carboxy indole, 5,6-dihydroxy-2-carbethoxy indole, 5,6-dihydroxy-2-carboxy indole, 5,6-dibenzyloxy-2-methyl indole, 5,6-dihydroxy-2-methyl indole, 5,6-dibenzyloxy-3-methyl indole, 5,6-dihydroxy-3-methyl indole, (5 or 6)-formyloxy-(6 or 5)-hydroxy indole, (5 or 6)-acetoxy-(6 or 5)-formyloxy indole, 6-formyloxy-5-methoxy indole, 6-benzyloxy-5-butoxy indole, 5-butoxy-6-hydroxy indole, 5-benzyloxy-6-butoxy indole, 6-butoxy-5-hydroxy indole, (5 or 6)-hydroxy-(6 or 5)-trimethylsilyloxy indole, 5,6-ditrimethylsilyloxy indole, 5,6-[1,1-(1-ethoxy ethyl)dioxy]indole, cyclic 5,6-dihydroxy phosphodiester indole, 5,6-thiocarbonyldioxy indole, 5-methoxy-6-trimethylsilyloxy indole, 5,6-di(trimethylsilyloxy)-2-methyl indole, 5,6-carbonyldioxy-2-methyl indole, (5 or 6)-hydroxy-(6 or 5)-myristoyloxy indole, 5,6-dimyristoyloxy indole, (5 or 6)-hydroxy-(6 or 5)-oleoyloxy indole, 5,6-dioleoyloxy indole, 5,6-di(trimethylsilyloxy)-2-carbethoxy indole, 5,6-di(trimethylsilyloxy)-2-trimethylsilyloxycarbonyl indole, 5,6-di(trimethylsilyloxy)-3-methyl indole, 6-hexadecoxy-5-methoxy indole, 6-hexadecoxy-5-hydroxy indole, 5-hexadecoxy-6-hydroxy indole, 5,6-dipivaloyloxy indole, (5 or 6)-hydroxy-(6 or 5)-pivaloyloxy indole, 5,6-dihexanoyloxy indole, (5 or 6)-hexanoyloxy-(5 or 6)-hydroxy indole, 5,6-dibutanoyloxy indole or (5 or 6)-butanoyloxy-(6 or 5)-hydroxy indole.

6. A method according to claim 1, wherein $R_4$ and $R_5$ are, independently of each other H,

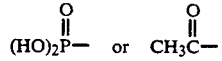

and $R_1$, $R_2$ and $R_3$ are all H.

7. A method according to claim 1, wherein the composition is in the form of a lotion, a gel, an emulsion, a balm, a stick, an oil, a milk, a cream, an ointment or a dusting powder.

8. A method according to claim 1 wherein the composition comprises one or more additives selected from the group consisting of solvents, thickeners, softeners, moisturizers, sealers, emollients, wetting agents, chelating agents, preservatives, anti-foaming agents, perfumes and emulsifiers.

9. A method according to claim 8, wherein the solvent is selected from the group consisting of alcohols, distilled water, deionized water, physiological saline solutions and glycols.

10. A method according to claim 9, wherein the alcohol is selected from the group consisting of ethanol, isopropyl alcohol and benzyl alcohol.

11. A method according to claim 9, wherein the glycol is selected from the group consisting of ethylene glycol, propylene glycol, dipropylene glycol and tripropylene glycol.

12. The method according to claim 1, wherein the composition is applied to skin.

* * * * *

UNITED STATES PATENT AND TRADEMARK OFFICE
CERTIFICATE OF CORRECTION

PATENT NO. : 5,126,125
DATED : June 30, 1992
INVENTOR(S) : John M. Pawelek

It is certified that error appears in the above-identified patent and that said Letters Patent is hereby corrected as shown below:

Title Page &  [54] Invention: Line 3 delete "DIHYDROXINDOLE " and sub-
Col. 1, line 3       stitute -- DIHYDROXYINDOLE --

Col. 14, line 4  Delete " claim 4 " and substitute -- claim 1 --

Signed and Sealed this

Eighth Day of February, 1994

Attest:

BRUCE LEHMAN

Attesting Officer    Commissioner of Patents and Trademarks